United States Patent
Hogan

(10) Patent No.: US 7,486,405 B2
(45) Date of Patent: Feb. 3, 2009

(54) OPTIMIZED REFERENCE LEVEL GENERATION

(76) Inventor: Josh N. Hogan, 620 Kingswood Ave., Los Altos, CA (US) 94022

( * ) Notice: Subject to any disclaimer, the term of this patent is extended or adjusted under 35 U.S.C. 154(b) by 106 days.

(21) Appl. No.: 11/789,278

(22) Filed: Apr. 23, 2007

(65) Prior Publication Data
US 2007/0252999 A1   Nov. 1, 2007

Related U.S. Application Data

(60) Provisional application No. 60/796,571, filed on May 1, 2006.

(51) Int. Cl.
*G01B 11/02* (2006.01)
(52) U.S. Cl. ...................... 356/497; 356/479
(58) Field of Classification Search ................ 356/479, 356/497
See application file for complete search history.

(56) References Cited

U.S. PATENT DOCUMENTS

| | | | | |
|---|---|---|---|---|
| 5,781,297 | A | * | 7/1998 | Castore ...................... 356/486 |
| 2004/0233457 | A1 | * | 11/2004 | Podoleanu et al. .......... 356/479 |
| 2007/0278389 | A1 | * | 12/2007 | Ajgaonkar et al. .......... 250/221 |

* cited by examiner

*Primary Examiner*—Tarifur Chowdhury
*Assistant Examiner*—Jonathon D Cook

(57) ABSTRACT

A method, apparatus and system for optimizing the magnitude of reference levels in non-invasive imaging and analysis is disclosed. Optimizing the magnitude of reference levels enables improving signal to noise ratios and thereby improving the sensitivity and performance of the imaging and analysis system. The invention includes dynamically modifying the magnitude of one or more reference beams and significantly reducing the magnitude of undesirable reference radiation components. It may further include one or more stabilizing feedback systems.

12 Claims, 6 Drawing Sheets

OPTIMIZED REFERENCE LEVEL GENERATION

CROSS REFERENCES TO RELATED APPLICATIONS

This utility patent application 11/789,278 claims priority from provisional application No. 60/796,571, filed on 1st. May 2006 the entirety of which is incorporated by reference as if fully set forth herein.

FIELD OF THE INVENTION

The invention relates to non-invasive imaging and analysis and in particular to optical imaging and analysis of defects or malignant aspects of targets such as cancer in skin or human tissue or manufacturing defects in components for improved quality control. This invention also relates to non-invasive analysis of concentrations of specific components or analytes in a target.

BACKGROUND OF THE INVENTION

This application involves non-invasive analysis of targets and relates to U.S. utility patent 11/048,694 filed on 31st. Jan. 2005 titled "Frequency Resolved Imaging", which is a continuation in part of U.S. utility patent application Ser. No. 11/025,698 filed on 29th. Dec. 2004 titled "A Multiple Reference Analysis System", the contents of both of which are incorporated herein by reference as if fully set forth herein. This application also relates to U.S. utility patent 11/254,965 filed on 19th. Oct. 2005 titled "Correlation of concurrent non-invasively acquired signals" the contents of which are incorporated herein by reference as if fully set forth herein.

Non-invasive analysis is a valuable technique for acquiring information about systems or targets without undesirable side effects, such as damaging the target or system being analyzed. In the case of analyzing living entities, such as human tissue, undesirable side effects of invasive analysis include the risk of infection along with pain and discomfort associated with the invasive process. In the case of quality control, it enables non-destructive imaging and analysis on a routine basis.

Optical coherence tomography (OCT), is a technology for non-invasive imaging and analysis. OCT typically uses a broadband optical source, such as a super-luminescent diode (SLD), to probe and analyze or image a target. It does so by applying probe radiation from the optical source to the target and interferometrically combining back scattered probe radiation from the target with reference radiation also derived from the optical source.

The typical OCT optical output beam has a broad bandwidth and short coherence length. The OCT technique involves splitting the output beam into a probe and reference beam, typically by means of a beam splitter, such as a pellicle, a beam splitter cube or a fiber coupler. The probe beam is applied to the system to be analyzed (the target). The reference beam is typically reflected back to the beam splitter by a mirror. Light scattered back from the target is combined with the reference beam in the beam splitter to form the measurement signal. Because of the short coherence length only light that is scattered from a depth within the target whose optical path length is substantially equal to the path length of the reference combine interferometrically. Thus the interferometric signal provides a measurement of the scattering value at a particular depth within the target. By varying the magnitude of the reference path length, a measurement of the scattering values at various depths can be determined and thus the scattering value as a function of depth can be determined, i.e. the target can be scanned.

In order to optimize the signal to noise ratio of the OCT imaging and analysis system the magnitude of the reference beam should be arranged to be compatible with the magnitude of the back scattered optical signal. This is typically achieved in conventional OCT systems by including a fixed attenuation element in the reference beam path. This technique is described in the paper titled "A Simple Intensity Noise Reduction Technique for Optical Low-Coherence Reflectometry" by authors W. V. Sorin and D. M. Baney published in IEEE PHOTONICS TECHNOLOGY LETTERS, Vol. 4, No. 12, Pages 1404-1406, December 1992.

The magnitude of the lixed attenuator is typically selected to attenuate the reference beam that is combined with the back-scattered probe signal to a level that is not significantly higher than the maximum back scattered probe signal. However the magnitude of the optical signal back-scattered from within the target decreases rapidly (typically approximately logarithmically) with increasing depth. Therefore with the conventional fixed attenuation approach the reference beam has an increasingly higher level with respect to back-scattered signals from increasing depths consequently the OCT signals associated with increasingly deeper regions within the target have increasingly reduced signal to noise ratio.

Furthermore in non-invasive imaging and analysis systems that use multiple reference beams, such as those described in application Ser. Nos. 11/025,698, 11/048,694, 11/254,965 incorporated herein by reference, there is typically a significant portion of the reference radiation reflected back to the beam splitter by the partial reflective element involved in generating the multiple reference beams. This component of the reference radiation that is reflected from the partial reflecting element introduces additional significant noise that degrades the signal to noise ratio.

Typically the magnitude of the reference radiation reflected from the partial reflecting element has a higher power level than the power levels of the multiple reference signals. Therefore introducing a fixed attenuator to reduce the magnitude of the radiation reflected from the partial reflecting element is not practical because it will attenuate the multiple reference signals by a corresponding amount.

There is therefore an unmet need for a method and apparatus for optimizing the level of the reference radiation or components of the reference radiation in order to enhance the signal to noise ratios and thereby improve system performance for both conventional OCT systems and multiple reference non-invasive analysis systems.

SUMMARY OF THE INVENTION

The invention provides a method, apparatus and system for optimizing the magnitude of reference levels in non-invasive imaging and analysis in order to improve signal to noise ratios and thereby improve the sensitivity and performance of the imaging and analysis. The invention includes dynamically modifying the magnitude of one or more reference beams and significantly reducing the magnitude of undesirable reference radiation components. It further includes one or more stabilizing feedback systems.

DETAILED DESCRIPTION OF THE INVENTION

Figure 1:
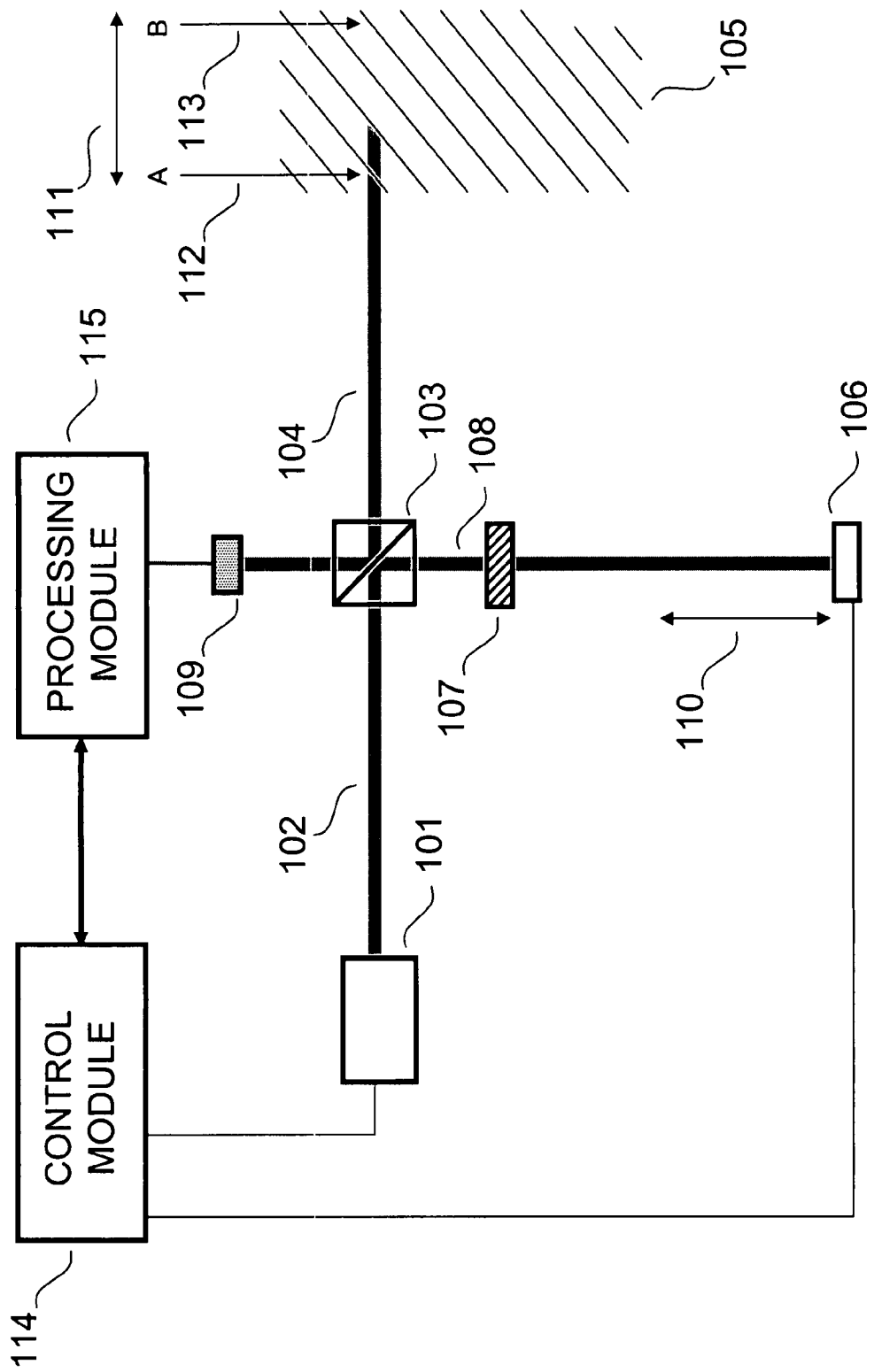
FIG. 1 is an illustration of a prior art conventional OCT system including a fixed attenuator in the reference beam path.

A conventional OCT system is illustrated in FIG. 1 where a broadband optical source 101, such as a superluminescent diode (SLD) with a collimated output, generates a broadband (wide spectral range) beam or radiation 102 which is applied to a beam-splitter 103. A portion of the broadband radiation, referred to as the probe beam or reference radiation, is applied to the target 105 where some of it will be back-scattered to the beam-splitter 103 and is referred to as back-scattered radiation 104.

A second portion of the broadband radiation 102 is directed by the beam-splitter 103 to a reference mirror 106 which reflects the radiation back to the beam-splitter 103. In typical (prior art) conventional OCT systems the reference path also includes an attenuator 107 which significantly reduces the magnitude of the radiation 108 returned to the beam-splitter 103. This attenuated returned radiation 108 is referred to as reference radiation.

The reference radiation 108 is combined with the back-scattered probe radiation 104 in the beam-splitter 103 to form the interferometric signal that is detected by the opto-electronic detector 109. The detected interferometric signal provides information about a specific region within the target such that the optical path length to the specific region is substantially equal to the optical path length to the reference mirror.

A conventional OCT system scans the target by translating the reference mirror. In the illustrated system translating the reference mirror 106 through a distance indicated by 110 would scan a corresponding region of the target 111. The extremes of the scanned portion of the target are further indicated by the A arrow 112 toward the front of the target and the B arrow 113 indicating the deepest region scanned. The position of the mirror 106 as drawn corresponds to the portion of the target indicated by the B arrow 113.

The reference mirror can be translated by conventional electromechanical means that is typically controlled by an electronic control module 114. While the reference mirror is translated the detected interferometric signal is typically acquired and processed by an electronic control module 115. The processed signal is typically made available for display, further processing or storage.

In a conventional OCT system the fixed value attenuator 107 can be selected to provide optimum signal to noise ratio for only one region of the target. For example if the attenuator were optimized for a signal corresponding to the region indicated by the A arrow of FIG. 1, it would not be optimized for the region indicated by the B arrow, which can have a significantly different signal level. Furthermore any overall change in the reflectivity of the target (for example due to a change in orientation of the front surface) can also adversely affect the signal to ratio for all regions.

Thus in conventional OCT systems (such as that illustrated in FIG. 1 and similar fiber based OCT systems) the use of a fixed attenuation of the reference beam represents a significant limitation in achievable signal to noise ratio which limits the performance that is achievable by the imaging and analysis system. The present invention is a novel approach, which addresses signal to noise limitations in conventional OCT and also to multiple reference imaging and analysis systems.

The invention involves generating a reference radiation whose level can be dynamically modified to optimize the signal to noise ratio by means of a dynamically variable attenuation reflective element. It also includes significantly reducing the level of unwanted components of reference radiation composite radiation composed of multiple components.

A preferred embodiment of this invention is illustrated in and described with reference to FIG. 2 where an OCT system is shown that in some respects is similar to the system described in FIG. 1 however the reference mirror of FIG. 1 is replaced with a variable attenuation reflective element 206 whose attenuation is controlled by the electronic control module 214 by means of an additional control signal 216. The preferred embodiment may also include an additional feedback signal 217 to stabilize the variable attenuation reflective element.

The preferred embodiment has a broadband optical source 201, such as an SLD which, generates broadband collimated output radiation 202 which is applied to a beam-splitter 203. A portion of the broadband radiation, referred to as probe radiation, is applied to the target 205 where some of it will be back-scattered to the beam-splitter 203 and is referred to as back-scattered radiation 204.

Figure 3:
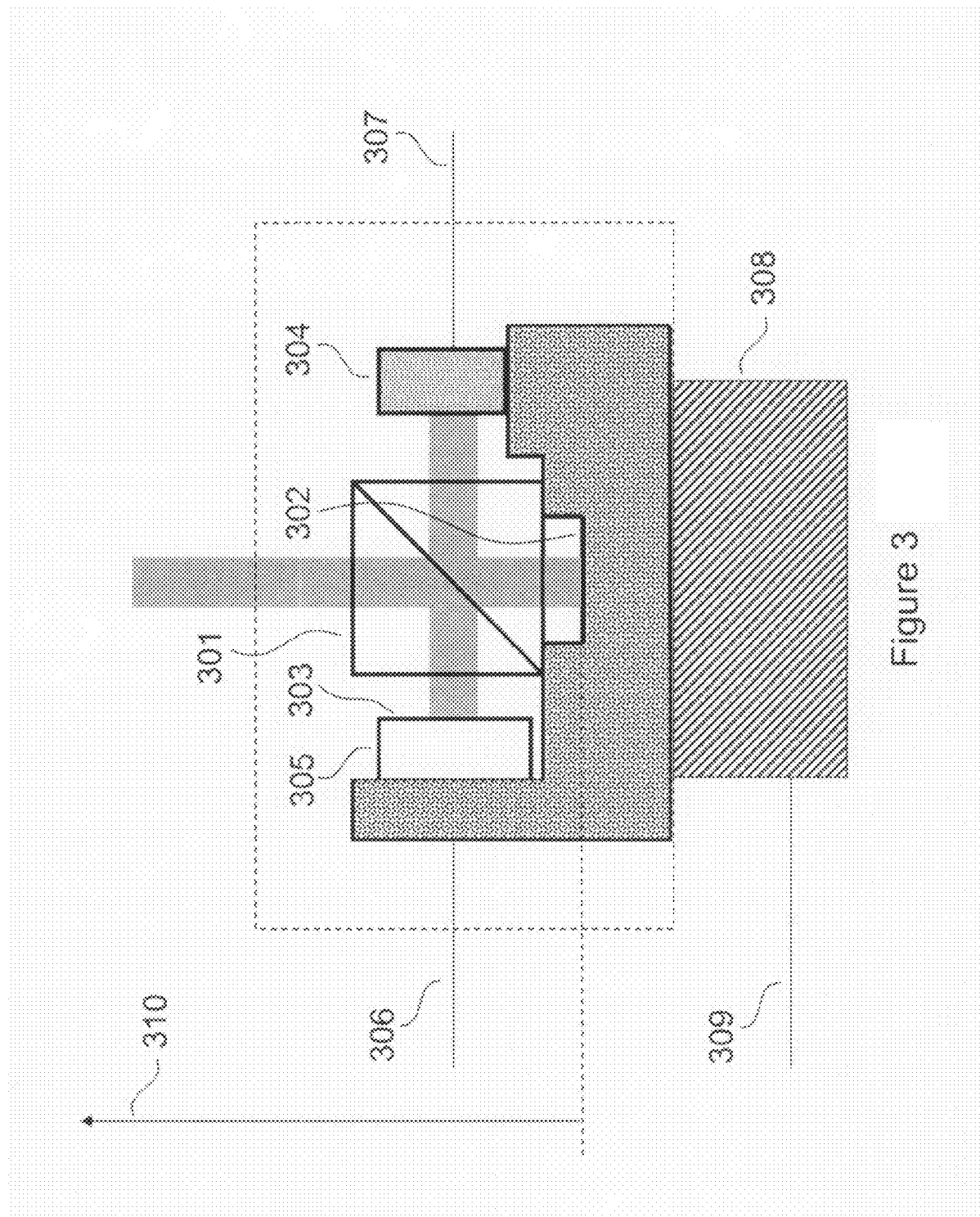
FIG. 3 is a more detailed illustration of a dynamically variable attenuation element.

A second portion of the broadband radiation 202 is directed by the beam splitter 203 to a variable attenuation reflective element 206 which is described in more detail in FIG. 3. The variable attenuation reflective element 206 reflects attenuated radiation back to the beam-splitter 203. As in conventional OCT systems the reference path may also include an attenuator 207 which significantly reduces the magnitude of the radiation 208 returned to the beam-splitter 203. This attenuated returned radiation 208 is referred to as reference radiation.

The reference radiation 208 is combined with the back-scattered probe radiation 204 in the beam-splitter 203 to form the interferometric signal that is detected by the opto-electronic detector 209. The detected interferometric signal provides information about a specific region within the target such that the optical path length to the specific region is substantially equal to the optical path length to the reference mirror.

The OCT system scans the target by translating the variable attenuation reflective element. In the illustrated system translating the variable attenuation reflective element 206 through a distance indicated by 210 would scan a corresponding region of the target 211. The extremes of the scanned portion of the target are further indicated by the A arrow 212 toward the front of the target and the B arrow 213 indicating the deepest region scanned. Translating the variable attenuation reflective element effectively modulates the reference radiation (to generate an interference signal).

The variable attenuation reflective element can be translated by conventional electromechanical means that is typically controlled by an electronic control module 214. While the variable reflective element is translated the detected interferometric signal is typically acquired and processed by an electronic control module 115. The processed signal is typically made available for display, further processing or storage.

As the variable attenuation reflective element 206 is translated to scan different regions within the target the effective reflectivity of the variable attenuation reflective element 206 is dynamically modified to optimize the signal to noise ratio for the specific region being scanned. For example, the effective reflectivity could be reduced when scanning the region indicated by the B arrow 213 compared to the effective reflectivity when scanning the region indicated by the A arrow 212.

By dynamically varying the attenuation of the reference radiation in a manner that is related to the depth at which the target is being analyzed greater signal to noise ratios and hence increased sensitivity can be achieved. Therefore the dynamically attenuated reference radiation whose attenuation is dynamically varied in a manner that is synchronously related to the modulation of the reference radiation enables an increased sensitivity non-invasive analysis system.

The magnitude of the attenuation of the dynamically attenuated reference radiation may be either increased or decreased for signals related to deeper regions of the target depending on the specific implementation and application. Furthermore any overall change in the reflectivity of the target (for example due 1:0 a change in orientation of the front surface) can be compensated for by further modifying the reflectivity of the variable attenuation reflective element thereby enabling dynamically optimizing the signal to noise ratio and hence system performance.

The variable attenuation reflective element 206 of the preferred embodiment is described in more detail in FIG. 3 where an additional beam-splitter 301 directs a first portion of the reference radiation to a first reflective surface 302 and a second portion of the reference radiation to a second reflective surface 303. The radiation reflected from these two reflective surfaces are combined interferometrically in the beam-splitter 301. The phase relationship between the radiation reflected from the two reflective surfaces 302 and 303 determines how much radiation is directed towards the additional opto-electronic detector 304.

The second reflective surface 303 is mounted on a piezo device whose length is controlled by a control signal 306 to modify the phase relationship between the radiation reflected from the two reflective surfaces 302 and 303 and thereby the amount of radiation is directed towards the additional opto-electronic detector 304. This also therefore modifies the magnitude of the usable reference radiation (the radiation returned to the beam-splitter 203 of FIG. 2).

The control signal 306 effectively modifies the attenuation of the reference radiation. By monitoring the output of the detector 304 by means of the detected signal 307 the magnitude of the attenuation of the reference radiation can be monitored and therefore modified in a controlled and stabilized manner. In this embodiment the dynamic attenuation is being accomplished using an interferometrically based variable attenuation reflective element.

In the preferred embodiment the variable attenuation reflective element described above is mounted on a conventional electro-mechanical translation mechanism (such as a voice coil or amplified piezo device) 308. The translation is determined by a control signal 309 which causes the variable attenuation reflective element to be translated through, for example, a range indicated by 310, which corresponds to 210 of FIG. 2. This corresponds to scanning the target from the region indicated by the B arrow to the A arrow.

Figure 2:
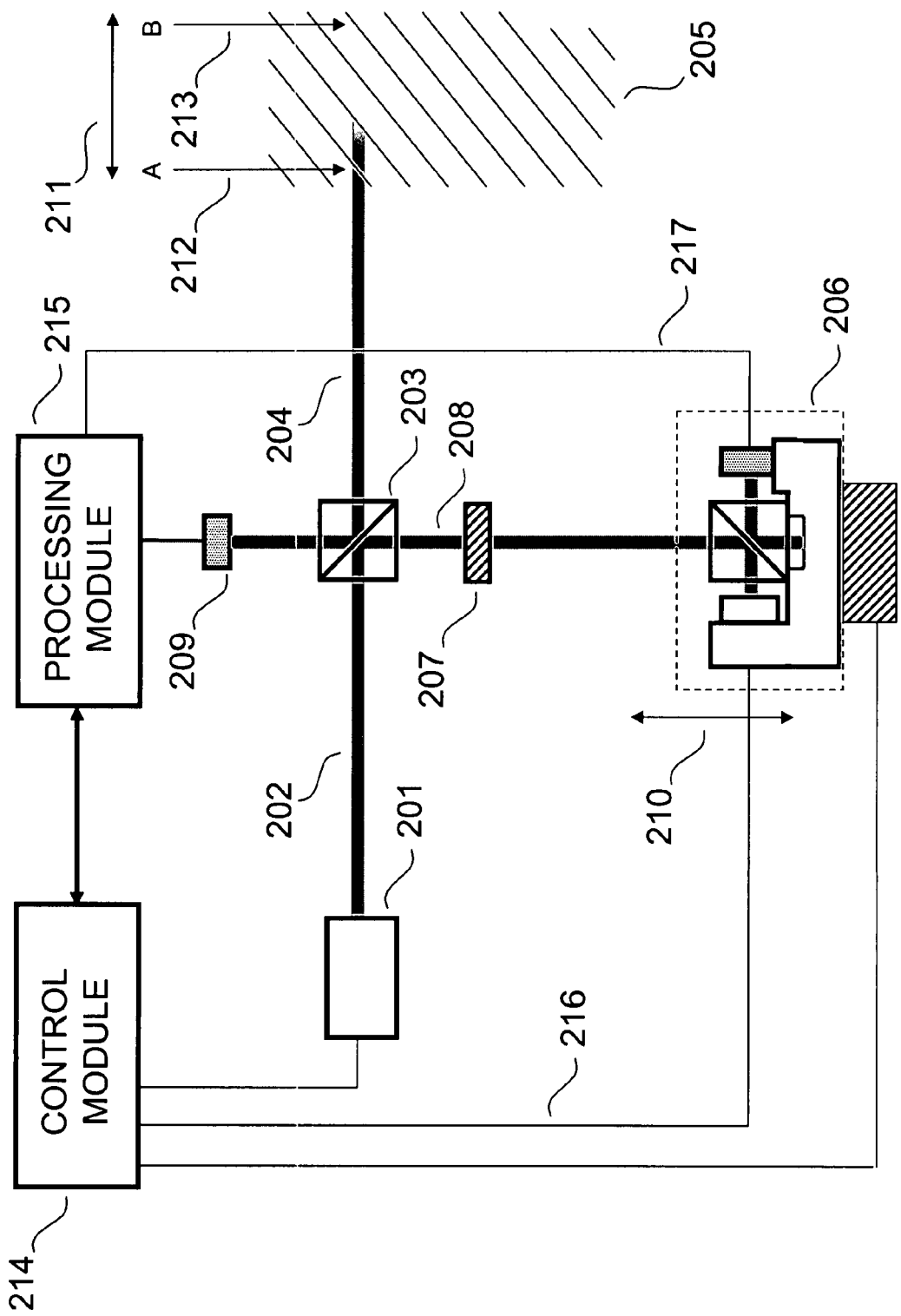
FIG. 2 is an illustration of the optimized reference generator for conventional OCT systems according to the invention.

During the scan indicated by 310 the variable attenuation reflective element would be varied from one attenuation level when acquiring a signal from deep within the target (arrow B of FIG. 2) to another attenuation level when acquiring a signal from a les deep region within the target (arrow A of FIG. 2).

Furthermore the nature of this variation can match the attenuation of the signals back scattered from the target. For example the attenuation may be varied in a logarithmic manner and thereby optimize the signal to noise ratio of the analysis system.

Figure 4:
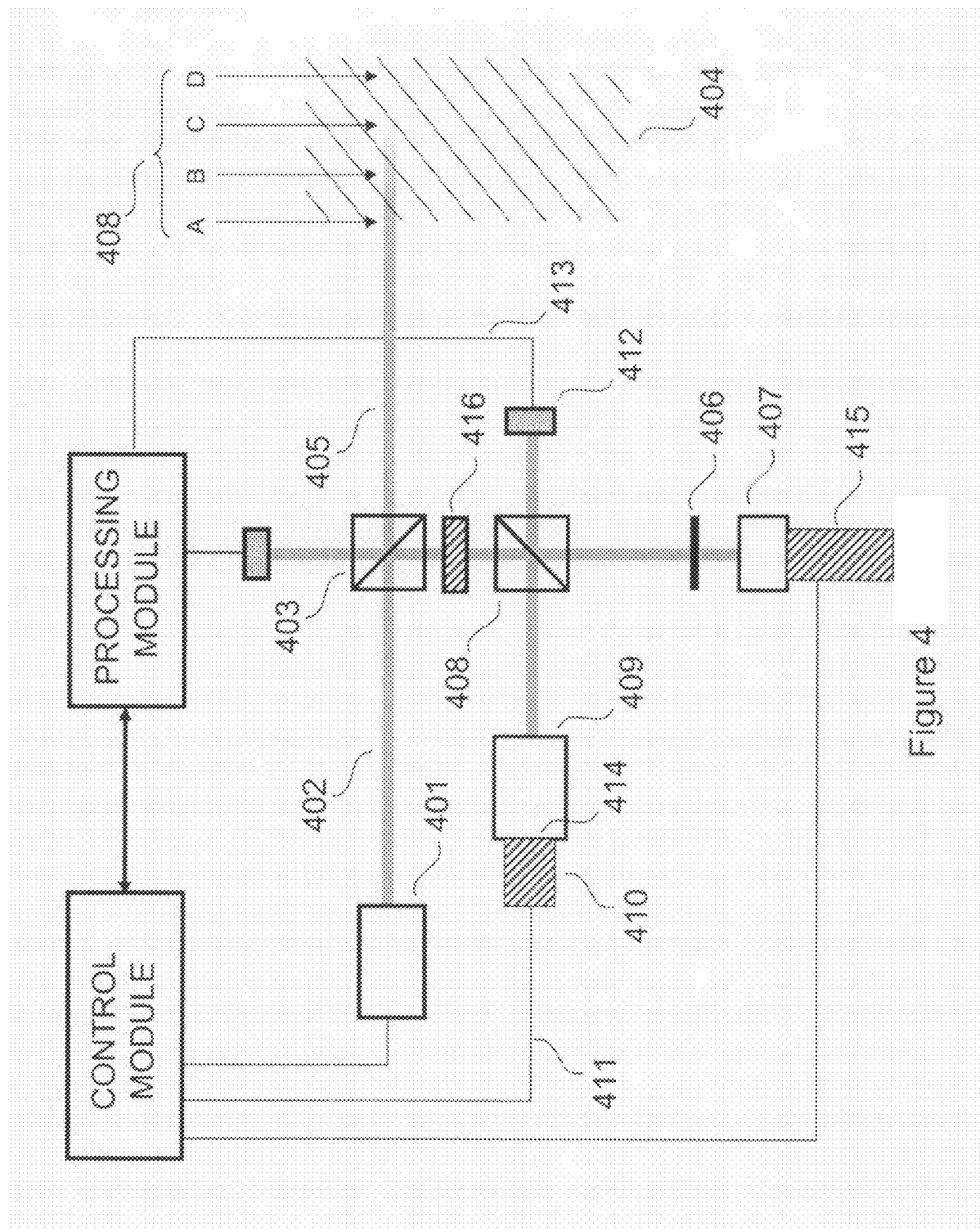
FIG. 4 is an illustration of the optimized reference generator for multiple reference analysis systems according to the invention.

A preferred embodiment of the invention applied to a frequency resolved imaging and analysis system (or multiple reference non-invasive analysis system), such as that described in application Ser. Nos. 11/025,698 and 11/048,694 incorporated herein by reference, is illustrated in and described with respect to FIG. 4 where a broadband optical source 401, such as an SLD, generates broadband collimated output radiation 402 which is applied to a beam-splitter 403. A portion of the broadband radiation, referred to as the probe radiation, is applied to the target 404 where some of it is back-scattered to the beam-splitter 403 and is referred to as back-scattered radiation 405.

A second portion of the broadband radiation 402 is directed by the beam-splitter 403 to a composite reference radiation generator that consists of a partial reflective element 406 and a modulated reflective element 407. This arrangement generates composite reference radiation consisting of multiple component radiation (or component reference radiation) which can generate multiple interference signals corresponding to multiple depths within the target in a manner that allows the different signals to simultaneously detected and separated electronically based on their having different frequency content (as described in the references incorporated herein).

The partial reflective element 406 reflects a substantial amount of reference radiation (which can be of the order of 80% or more, depending on the target) radiation back to the beam-splitter 403. In this arrangement using a fixed attenuator to reduce (or remove) this large component reflected by the partial reflective element may not be appropriate as such an attenuator would also attenuate the desired components of the multiple reference radiation.

In this preferred embodiment a second beam-splitter 408 directs a portion of the radiation to a reflective element 409. The path length from the beam-splitter 408 to the reflective element 409 is substantially the same as the path length from the beam-splitter 408 to the partial reflective element 406. The radiation reflected from the reflective element 409 combines interferometrically with the radiation reflected from the partial reflective element 406.

The relative phase relationship between the radiation reflected from the reflective element 409 and the radiation reflected from the partial reflective element 406 can be controlled by translating the reflective element 409 (or the partial reflective element 406). In the preferred embodiment this is accomplished by mounting the reflective element 409 on a piezo device 410 and controlling the length of the piezo device 410 by means of a control signal 411.

The piezo device 410 can be controlled to adjust the relative phase relationship so that the radiation from both the partial reflective element 406 and the reflective element 409 is substantially all directed towards the opto-electronic detector 412 thereby removing the unwanted reference radiation component from the composite reference radiation returned to the beam-splitter 403 to generate the multiple depth related interferometric signals, herein referred to as a composite interference signal, with improved signal to noise ratio and hence increased sensitivity.

In this embodiment the elimination or attenuation of unwanted reference radiation by selectively attenuating at least one component of the reference radiation is accomplished using an interferometrically based approach. The optimum phase relationship between the radiation reflected from the reflective element 409 and the radiation reflected from the partial reflective element 406 can be maintained by modifying the piezo control signal 411 and monitoring the detected signal 413.

For example the piezo length could be systematically increased or decreased by a small amount during the times when the scanning system is near the extremes of the scan synchronously with the scan drive signal. If the phase relationship is optimal the detected signal will decrease when the piezo length is either increased or decreased. Therefore the detected signal and the control signal can be used to form a feedback system to maintain an optimum phase relationship during the non-extreme portions of the scan.

Alternatively or additionally a high frequency dither could be imposed my modulating the radiation reflected from the reflective element 409 (or the partial reflective element 406). This could be accomplished by modulating the piezo device. As an alternative to a piezo device a phase modulator could be used for both the synchronous optimizing approach and the high frequency dither approach.

Typically the reflective element 409 will have a reflectivity similar to that of the partial reflective element 406 and therefore will also be a partial reflective element. This enables generating one or more additional reflections by means of the rear surface 414 of the reflective element 409. The optical path length from the front surface of the reflective element 409 to the rear surface 414 determines whether any additional interference signals generated between reflections from the multiple reference generator (reflective elements 406 and 407) and reflections from the rear surface 414.

For example a relatively long optical path length from the front surface of the reflective element 409 to the rear surface 414 could be selected to generate an additional high order (high frequency) interference signal to be detected by detector 412. Such a high order interference signal could be selected to correspond to a region within the target that is too deep to generate a usable interference signal from the back-scattered probe signal.

Therefore such an arrangement would not decrease the analysis capability of the system but would enable monitoring and dynamically optimizing the alignment and spacing of the elements 406 and 407. The long optical path length from the front surface of the reflective element 409 to the rear surface 414; the relatively short separation between elements 406 and 407; and the magnitude of the translation scan of the piezo device 415 could be selected such that more than one additional high order (high frequency) interference signal will be detected by detector 412.

The detection of more than one high order (high frequency) interference signal by detector 412 enables accurate monitoring and alignment of spacing and orientation of the reflective elements 406 and 407. Furthermore this alignment optimization can be performed during operation of the system. Many alternative implementations of these alignment and stabilization techniques are possible.

The relative levels of the desired components of the composite reference radiation may be optimized by selecting the reflectivities of the reflective elements 406 and 407. This selection may include having one or more components of the composite reference radiation having levels that are less than optimum for analyzing their associated depth regions, such as lower than the level of the back scattered radiation from the associated depth region. This may therefore yield reduced but valuable information, such as location information only for these regions with inaccurate or clipped intensity information. In some applications (for example requiring a relatively low value partial reflector 406 and a small number of component in the reference radiation) reflectivities may be such that use of an additional fixed attenuator 416 may be appropriate.

Figure 5:
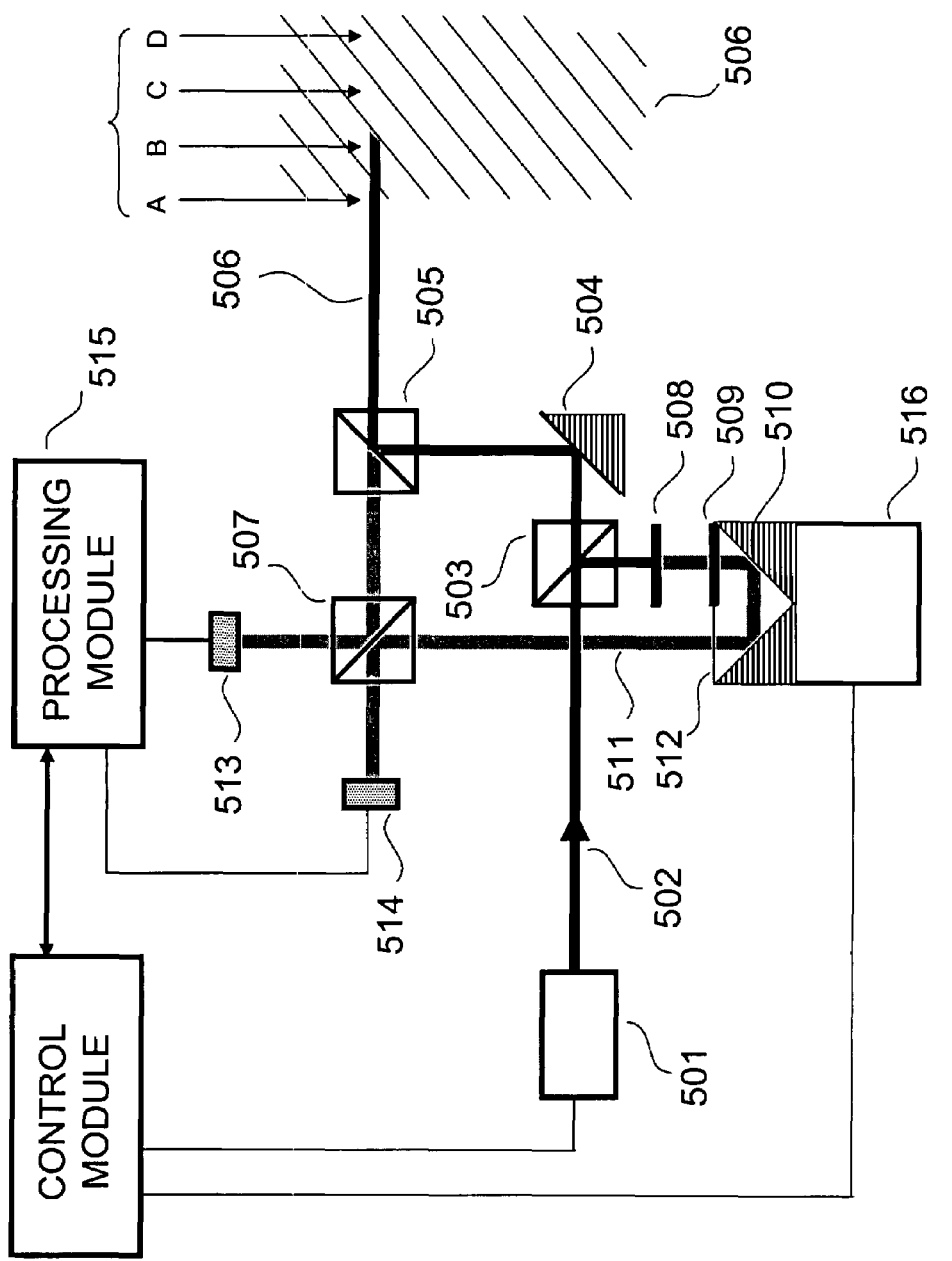
FIG. 5 is an illustration of a transmissive embodiment of the invention.

An alternative embodiment of the invention applied to a transmissive composite reference non-invasive analysis system is illustrated in and described with respect to FIG. 5 where a broadband optical source 501, such as an SLD, generates broadband collimated output radiation 502 which is applied to a beam-splitter 503. A portion of the broadband radiation is directed by reflective element 504 to a second beam-splitter 505 which applies a portion of the radiation, referred to as probe radiation, to the target 506 where some of it is back-scattered to the beam-splitter 505 and is referred to as back-scattered radiation 506.

A portion of this back-scattered radiation is transmitted through the beam-splitter 505 to a third beam-splitter 507. A second portion of the broadband radiation 502 is directed by the beam-splitter 503 to a transmissive composite reference radiation generator that consists of a partial transmissive elements 508 and 509 which can have transmissivities (i.e. percentage of radiation transmitted) of the order of 20%. In this embodiment the partial transmissive element 509 is attached to a region of the surface of a retro-reflector 510 which is mounted on a modulating piezo device 516.

The transmissive composite reference radiation 511 is generated by multiple reflections between the partial transmissive elements 508 and 509. The relative levels of the components of the composite reference radiation are determined by the reflectivities of the partial transmissive elements 508 and 509 which may be selected to match the back-scatter profile of the target 506.

The transmissive composite reference radiation 511 emerges from an anti-reflection coated region of the retro-reflector 510 and is directed towards the third beam-splitter 507 where it is combined with a portion of the back-scattered probe radiation to generate complementary interference signals which are detected by a pair of electro-optic detectors 513 and 514. The outputs of these detectors 513 and 514 are processed by the electronic processing module 515, typically in a balanced detector configuration, to separate and analyze the composite interferometric signal, i.e. the multiple interferometric signals corresponding to multiple depths within the target, such as indicated by the arrows A, B, C and D.

The transmissive composite reference radiation generated by the partial transmissive elements 508 and 509 and the piezo device 516 does not have a large magnitude unwanted component. Therefore levels of the components of the generated composite reference radiation for optimum signal to noise ratios for a particular target can be determined by an appropriate selection of the transmissivities and reflectivities of the partial transmissive elements 508 and 509.

This enables the components of the transmissively generated composite reference radiation to be matched to the scattering characteristics of the target to provide a non-invasive analysis system with optimized signal to noise ratio and the hence optimized sensitivity of the non-invasive analysis system. Such an optimized non-invasive analysis system with a transmissive composite reference radiation generator and be used for non-invasive imaging and analysis of targets (as described in the applications incorporated by reference) including non-invasive analysis of tissue to image the tissue or to determine a measurement of an analyte, such as, the concentration level of glucose in tissue where the simultaneously or concurrently acquired information from multiple depths within the target can be processed.

Figure 6:
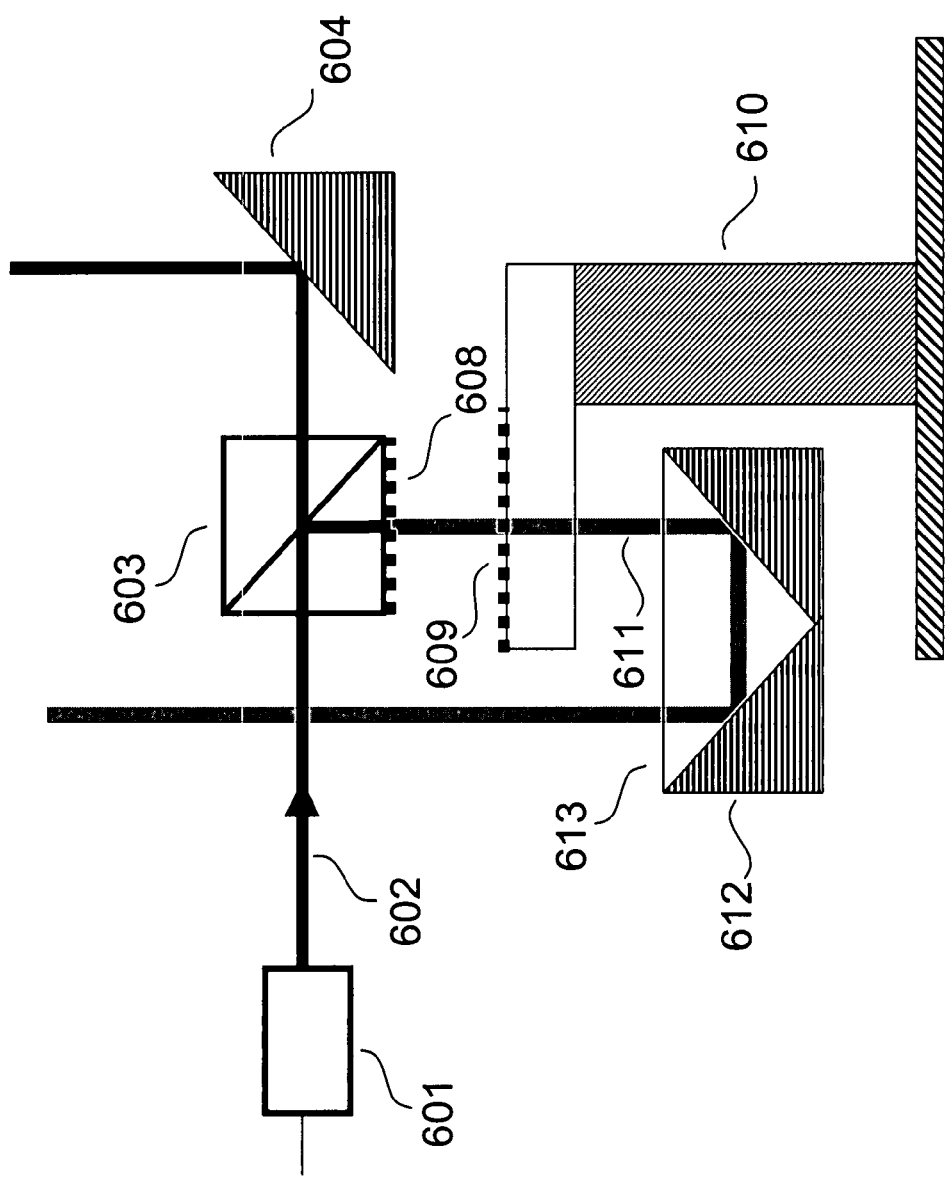
FIG. 6 is an illustration of the an alternative transmissive embodiment of the invention.

There are many possible configurations of the transmissive composite reference radiation generator described above. For example an alternative configuration is illustrated in and described with respect to FIG. 6 where as before a broadband optical source 601, such as an SLD, generates broadband collimated output radiation 602 which is applied to a beam-splitter 603. A portion of the broadband radiation is directed by beam steering element 604 via a second beam-splitter to the target as before. For purposes of this invention, beam-splitters, mirrors, etc are referred to a components that separate, capture, combine or apply (direct) radiation.

A second portion of the broadband radiation 602 is directed by the beam-splitter 603 to a transmissive composite reference radiation generator that consists of partial transmissive elements 608 and 609 which have transmissivities of the order of 1% to 20%. In this embodiment the partial transmissive element 608 is a partial transmissive and reflective coating on the beam-splitter 603. The partial transmissive element 609 is one surface of an optical element which is mounted on a modulating piezo device 610 (which could be a ring piezo actuator with a through-hole). The other surface of the optical is anti-reflection coated.

The transmissive composite reference radiation 611 is generated by multiple reflections between the partial transmissive elements 608 and 609. The relative levels of the components of the composite reference radiation are as before determined by the transmissivities and reflectivities of the partial transmissive elements 608 and 609 which may be selected to match the nominal back-scatter profile of the target.

The transmissive composite reference radiation 611 emerges from an anti-reflection coated surface of the optical element containing the reflective surface 609 and is re-directed by the retro-reflector 612 (which also could be separate mirrors) towards the third beam-splitter as before. In this configuration the front surface 613 of the retro-reflector 612 is anti-reflection coated. Furthermore, the retro-reflector 612 is typically fixed or used for beam alignment purposes.

As before, the transmissive composite reference radiation generated by the partial transmissive elements 608 and 609 and the Piezo device 610 does not have a large magnitude unwanted component. Therefore levels of the components of the generated composite reference radiation for optimum signal to noise ratios, and hence sensitivity, for a particular target can be determined by an appropriate selection of the transmissivities and reflectivities of the partial transmissive elements 608 and 609.

It is understood that the above description is intended to be illustrative and not restrictive. Many of the features have functional equivalents that are intended to be included in the invention as being taught.

Many variations and combinations of the above embodiments are possible, for example, various combinations of modulators can be used, including but not limited to phase modulators and Piezo-electric modulators. Mechanically amplified Piezo-electric actuators (to increase length changes). In some embodiments the relative optical path lengths of reference beams could be systematically varied to vary the relative locations from which information is obtained.

Temperature control could be used to vary phase relationships to attenuate unwanted components. Precise manufacturing tolerances could be used to ensure appropriate phase relationships to selectively attenuate at least one (unwanted) component of composite reference radiation.

The preferred embodiments illustrated are free space configurations. Equivalent configurations could be implemented in optical fiber or in combinations of free space and optical fiber. In such designs or configurations beam-splitters could be replaced by fiber couplers. Mirrors could be replaced by fiber reflective elements, such as fiber loops or Bragg gratings.

Embodiments described using interferometrically based variable attenuation reflective elements could be transmissive elements. Rather than interferometrically based attenuation could be accomplished by other means, such as, liquid crystal variable attenuators, or electronically controlled micro-electro-mechanical systems (MEMS, micro-mirror arrays).

The preferred embodiments are described and illustrated with respect to an OCT system using a broadband optical source. The invention also applies to other versions of OCT including, but not limited to, Fourier and spectral domain OCT. The preferred embodiments are described and illustrated in terms of an optical processing system generating broadband optical probe and reference beams (or radiation), however the invention is not limited to optical radiation. The invention applies to all regions of the electromagnetic spectrum, including but not limited to, micro-wave or X-ray, and is not restricted to the region conventionally referred to as optical. The invention applies to other forms of radiation, including but not limited to acoustic radiation.

For example, an ultra-sound source of acoustic radiation with a broad spectral range could be used to generate the probe and reference beams (or radiation). Acoustic reflective elements and length modulators or acoustic modulating techniques could be used to generate the composite reference radiation along other acoustic elements including but not limited to acoustic lenses. The resulting ultra-sound system would constitute a non-invasive imaging and analysis system according to the invention.

For purposes of this invention a source of broadband radiation, includes but is not limited to, optical sources of, such as SLDs, mode-locked laser, LEDs, other regions of the electromagnetic spectrum and sources of acoustic radiation.

Many of the features have functional equivalents that are intended to be included in the invention as taught. For example, the optical source could include multiple SLDs with either over-lapping or non-overlapping wavelength ranges, or, in the case of a mode-locked laser source could be an optically pumped mode-locked laser, it could be a solid state laser, such as a Cr:LiSAF laser optically pumped by a diode laser.

The optical source could be an actively mode-locked laser diode or a passively mode locked by a Kerr lens or a semiconductor saturable absorber mirror. Gain switched optical sources, with optical feedback to lock modes may also be used. For purposes of this invention, mode-locked lasers will include gain switched optical sources. The optical source could be a VCSEL (vertical cavity surface emitting laser), or an LED (light emitting diode) or an incandescent or fluorescent light source or could be arrays of the above sources.

Other examples will be apparent to persons skilled in the art. The scope of this invention should be determined with reference to the specification, the drawings, the appended claims, along with the full scope of equivalents as applied thereto.

What is claimed is:

1. A method for increasing sensitivity of non-invasive analysis of a target, said method comprising:
   generating probe radiation and reference radiation;
   modulating said reference radiation;
   dynamically interferometrically attenuating said modulated reference radiation;
   applying said probe radiation to said target;

capturing at least part of said probe radiation scattered from within said target to form captured scattered probe radiation;

combining said captured scattered probe radiation and said attenuated modulated reference radiation to form an interferometric signal;

detecting said interferometric signal to form an electronic signal; and processing said electronic signal to achieve non-invasive analysis of said target whereby said non-invasive analysis has increased sensitivity.

2. The method of claim 1, wherein the dynamically attenuated reference radiation is dynamically attenuated in a manner that is synchronously related to the modulation of the reference radiation.

3. The method of claim 1, wherein the magnitude of the attenuation of the dynamically attenuated reference radiation varies in a manner related to the region of the target with which a signal is related.

4. A method for increasing sensitivity of non-invasive analysis of a target, said method comprising:

generating probe radiation and composite reference radiation;

modulating at least some component of said composite reference radiation;

selectively interferometrically attenuating at least one component of said composite reference radiation;

applying said probe radiation to said target;

capturing at least part of said probe radiation scattered from within said target to form captured scattered probe radiation;

combining said captured scattered probe radiation and said selectively attenuated composite reference radiation to form a composite interferometric signal;

detecting said composite interferometric signal to form an electronic signal; and processing said electronic signal to achieve non-invasive analysis of said target whereby said non-invasive analysis has increased sensitivity.

5. A system for increasing sensitivity of non-invasive analysis of a target, said system comprising:

a source operable to generate probe radiation and reference radiation;

a modulator operable to modulate said reference radiation;

an interferometric attenuating element operable to dynamically attenuate said modulated reference radiation;

components operable to apply said probe radiation to said target;

components operable to capture at least part of said probe radiation scattered from within said target to form captured scattered probe radiation;

components operable to combine said captured scattered probe radiation and said attenuated modulated reference radiation to form an interferometric signal;

a detector operable to detect said interferometric signal to form an electronic signal; and a processor operable to process said electronic signal to achieve non-invasive analysis of said target whereby said non-invasive analysis has increased sensitivity.

6. The system of claim 5, wherein the dynamically attenuated reference radiation is dynamically attenuated in a manner that is synchronously related to the modulation of the reference radiation.

7. The system of claim 5, wherein the magnitude of the attenuation of the dynamically attenuated reference radiation varies in a manner related to the region of the target with which a signal is related.

8. A system for increasing sensitivity of non-invasive analysis of a target, said system comprising:

a source operable to generate probe radiation and composite reference radiation;

a modulator operable to modulate at least some component of said composite reference radiation;

an interferometric attenuating element operable to selectively attenuate at least one component of said composite reference radiation;

components operable to apply said probe radiation to said target;

components operable to capture at least part of said probe radiation scattered from within said target to form captured scattered probe radiation;

components operable to combine said captured scattered probe radiation and said selectively attenuated composite reference radiation to form a composite interferometric signal;

a detector operable to detect said composite interferometric signal to form an electronic signal; and a processor operable to process said electronic signal to achieve non-invasive analysis of said target whereby said non-invasive analysis has increased sensitivity.

9. An apparatus for increasing sensitivity of non-invasive analysis of a target, said apparatus comprising:

means for generating probe radiation and reference radiation;

means for modulating said reference radiation;

means for dynamically interferometrically attenuating said modulated reference radiation;

means for applying said probe radiation to said target;

means for capturing at least part of said probe radiation scattered from within said target to form captured scattered probe radiation;

means for combining said captured scattered probe radiation and said attenuated modulated reference radiation to form an interferometric signal;

means for detecting said interferometric signal to form an electronic signal; and means for processing said electronic signal to achieve non-invasive analysis of said target whereby said non-invasive analysis has increased sensitivity.

10. The apparatus of claim 9, wherein the dynamically attenuated reference radiation is dynamically attenuated in a manner that is synchronously related to the modulation of the reference radiation.

11. The apparatus of claim 9, wherein the magnitude of the attenuation of the dynamically attenuated reference radiation varies in a manner related to the region of the target with which a signal is related.

12. An apparatus for increasing sensitivity of non-invasive analysis of a target, said apparatus comprising:

means for generating probe radiation and composite reference radiation;

means for modulating at least some component of said composite reference radiation;

means for selectively interferometrically attenuating at least one component of said composite reference radiation;

means for applying said probe radiation to said target;

means for capturing at least part of said probe radiation scattered from within said target to form captured scattered probe radiation;

means for combining said captured scattered probe radiation and said selectively attenuated composite reference radiation to form a composite interferometric signal;

detecting said composite interferometric signal to form an electronic signal; and means for processing said electronic signal to achieve non-invasive analysis of said target whereby said non-invasive analysis has increased sensitivity.

* * * * *